US010610307B2

United States Patent
Kotian et al.

(10) Patent No.: US 10,610,307 B2
(45) Date of Patent: Apr. 7, 2020

(54) WORKFLOW ASSISTANT FOR IMAGE GUIDED PROCEDURES

(71) Applicant: General Electric Company, Schenectady, NY (US)

(72) Inventors: Francois Kotian, Buc (FR); Thomas McCarthy, Paris (FR); Francisco Sureda, Buc (FR); Valerie Desnoux, Buc (FR)

(73) Assignee: General Electric Company, Schenectady, NY (US)

( * ) Notice: Subject to any disclaimer, the term of this patent is extended or adjusted under 35 U.S.C. 154(b) by 155 days.

(21) Appl. No.: 15/718,941

(22) Filed: Sep. 28, 2017

(65) Prior Publication Data
US 2019/0090954 A1 Mar. 28, 2019

(51) Int. Cl.
*A61B 34/00* (2016.01)
*A61B 34/20* (2016.01)
(Continued)

(52) U.S. Cl.
CPC ............ *A61B 34/20* (2016.02); *A61B 90/37* (2016.02); *A61B 90/96* (2016.02); *A61B 90/98* (2016.02); *G06N 20/00* (2019.01); *G16H 40/00* (2018.01); *G16H 70/20* (2018.01); *H04N 5/247* (2013.01); *A61B 34/25* (2016.02); *A61B 2017/00203* (2013.01); *A61B 2034/105* (2016.02); *A61B 2034/2057* (2016.02); *A61B 2034/2065* (2016.02); *A61B 2034/2074* (2016.02); *A61B 2090/365* (2016.02); *A61B 2090/371* (2016.02); *A61B 2090/372* (2016.02); *A61B 2090/373* (2016.02); *A61B 2090/376* (2016.02); *A61B 2090/502* (2016.02); *G06F 17/50* (2013.01)

(58) Field of Classification Search
CPC .... A61B 2034/2057; A61B 2034/2074; A61B 2090/373; A61B 34/20; A61B 90/37; G06F 17/50; G16H 40/00; G16H 70/20; H04N 5/247
See application file for complete search history.

(56) References Cited

U.S. PATENT DOCUMENTS 7,428,296 B2 9/2008 Bernhardt et al.
8,164,631 B2 4/2012 Klingenbeck-Regn
(Continued)

OTHER PUBLICATIONS

Bhatia, B., Oates, T., Xiao, Y., and Hu, P. 2007. Real-time identification of operating room state from video. In: Proceedings of the 19th Conference on Innovative Applications of Artificial Intelligence (IAAI). pp. 1761-1766.
(Continued)

*Primary Examiner* — Robert T Nguyen

(57) ABSTRACT

A workflow assistance system for image guided surgical procedures includes an interventional imaging system. The interventional imaging system operates to move relative to a patient and to acquire interventional images during a surgical procedure. A surveillance system is arranged about a surgical suite and produces surveillance data. A workflow controller processes the surveillance data to identify locations of clinicians, the patient, the interventional imaging system, and medical equipment within the surgical suite and provide operational commands to the interventional imaging system based upon the surveillance data.

15 Claims, 11 Drawing Sheets

(51) Int. Cl.
| | |
|---|---|
| *A61B 90/00* | (2016.01) |
| *A61B 90/96* | (2016.01) |
| *A61B 90/98* | (2016.01) |
| *H04N 5/247* | (2006.01) |
| *G16H 40/00* | (2018.01) |
| *G16H 70/20* | (2018.01) |
| *G06N 20/00* | (2019.01) |
| *A61B 17/00* | (2006.01) |
| *A61B 34/10* | (2016.01) |
| *A61B 90/50* | (2016.01) |
| *G06F 17/50* | (2006.01) |

(56) References Cited

U.S. PATENT DOCUMENTS

| | | | |
|---|---|---|---|
| 8,199,876 | B2 | 6/2012 | Graumann et al. |
| 8,611,499 | B2 | 12/2013 | Spahn |
| 9,433,395 | B2* | 9/2016 | Kang ............... A61B 6/544 |
| 9,589,336 | B2 | 3/2017 | Fkohr et al. |
| 9,642,584 | B2 | 5/2017 | Niebler et al. |
| 9,649,080 | B2 | 8/2017 | Kwak et al. |
| 2013/0083894 | A1* | 4/2013 | Niebler ............ A61B 6/4441 378/62 |
| 2014/0163736 | A1* | 6/2014 | Azizian ............ A61B 6/102 700/259 |
| 2016/0183903 | A1 | 6/2016 | Vandroux et al. |
| 2016/0379504 | A1* | 12/2016 | Bailey ............... G16H 40/63 434/219 |
| 2017/0035374 | A1* | 2/2017 | Schafer ............. A61B 6/02 |
| 2017/0194008 | A1 | 6/2017 | Vandroux et al. |
| 2017/0258417 | A1* | 9/2017 | Hoornaert ......... A61B 6/547 |
| 2019/0223961 | A1* | 7/2019 | Barral .............. A61B 34/25 |
| 2019/0328461 | A1* | 10/2019 | Kemp ............... G16H 30/40 |
| 2019/0380788 | A1* | 12/2019 | Becker ............. A61B 34/70 |
| 2019/0380793 | A1* | 12/2019 | Abovitz ............ A61B 90/37 |

OTHER PUBLICATIONS

Cook, Daniel, Wisconsin 'Black Box' Law Would Require Cameras in Every OR, Outpatient Surgery, Mar. 13, 2017.

Guglielmo, Wayne J, Cameras in the Operating Room: A New Problem for Docs?, Medscape, Sep. 30, 2015.

Jackman, Tom, Could cameras in operating rooms reduce preventable medical deaths?, The Washington Post, Aug. 25, 2015.

Maquet GmbH, Tegris Redefining OR Integration brochure, Feb. 2015.

Ladikos, A., Benhimane, S., and Navab, N. 2008b. Real-time 3d reconstruction for collision avoidance in interventional environments. In: International Conference on Medical Image Computing and Computer-Assisted Intervention (MICCAI). pp. 526-534.

White, Jess, Should cameras be installed in every operating room? Healthcare Business & Technology, Aug. 31, 2015.

Anonymous: "Kinect—Wikipedia", Aug. 27, 2012, retrieved from the Internet: URL: https://en.wikipedia.org/w/index.php?title-Kinect &oldid=509466481, retrieved on Feb. 12, 2019.

Comparetti, Mirko Daniele, et al., "Safe surgical robotic system and workflow design in the ACTIVE project for awake neurosurgery," Oct. 31, 2012.

EP Patent Application No. 18195875.2 Search Report dated May 31, 2019, 11 pages.

* cited by examiner

| | Buc Hospital | | Room R3060 | Patient ID 123456 | 2017/06/27 08:33:24 |
|---|---|---|---|---|---|
| | Object | | Position | Inferred role | Inferred action |
| 1 | Operator #1 | | ############ | Interventionalist | Guidewire introduction |
| 2 | | Hand #1 | ############ | | |
| 3 | | Hand #2 | ############ | | |
| 4 | | Gaze | ############ | | |
| 5 | Operator #2 | | | Assistant | Unknown |
| 6 | Operator #3 | | | Assistant | Unknown |
| 7 | Operator #4 | | ############ | Anesthesiologist | Patient surveillance |
| 11 | | Hand #1 | ############ | | |
| 15 | | Hand #2 | ############ | | |
| 16 | | Gaze | ############ | | |
| 17 | Patient | | ############ | | Not moving |
| 18 | C-arm | | ############ | | |
| 19 | Anesthesia machine | | ############ | | |
| 20 | Monitor #1 | | ############ | | |
| 21 | Monitor #2 | | ############ | | |
| 22 | Monitor #3 | | ############ | | |
| 23 | Monitir #4 | | ############ | | |
| 24 | Seringe | | | | |
| 25 | Introducer | | ############ | | |
| 26 | Guidewire | | ############ | | |

FIG. 6A

| Time | Event |
|---|---|
| ... | |
| 27/06/2017 07:15:08 | Nurse #4 leaves room |
| 27/06/2017 07:15:09 | Idle |
| 27/06/2017 08:05:13 | Stetcher in |
| ... | |
| 27/06/2017 08:25:45 | Exam start |
| ... | Digital assistant: "CPT 92920, non-severe lesion, stable patient: imaging system ready, predicted procedure duration: 35 minutes" |
| ... | |
| 27/06/2017 08:30:33 | Gantry rotated to CRA/CAU=0° LAO/RAO=0° |
| ... | |
| 27/06/2017 08:31:41 | Bar code scanning ########: guidewire xxxx |
| ... | |
| 27/06/2017 08:33:08 | Guidewire introduction by operator #1 |
| ... | |
| 27/06/2017 08:33:24 | Fluoro sequence start |
| 27/06/2017 08:33:25 | Guidewire tip detected in image, position #### |
| ... | |
| 27/06/2017 08:35:52 | Fluoro sequence stop |
| 27/06/2017 08:35:53 | Digital assistant "Recommended: move to CRA/CAU=12° LAO/RAO=-5°" |
| 27/06/2017 08:35:54 | Digital assistant "Predicted procedure completion: 08:59:00" |

FIG. 6B

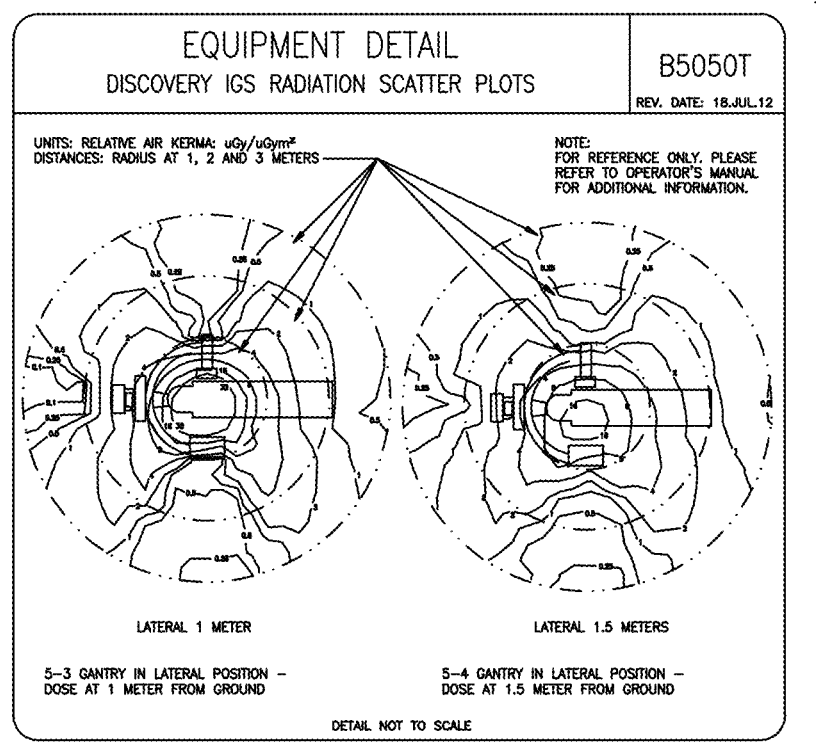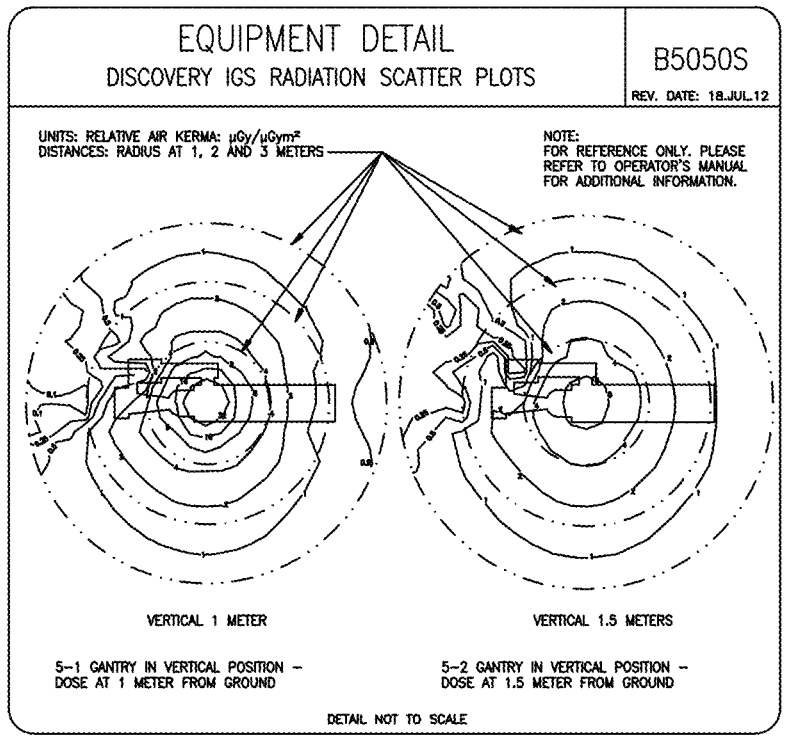
FIG. 8C

WORKFLOW ASSISTANT FOR IMAGE GUIDED PROCEDURES

BACKGROUND

The present disclosure relates to image guided procedures. More specifically, the present disclosure relates to automated workflow and procedure guidance in an image guided procedure. Surgical suites are often complex and crowded environments in which multiple caregivers and multiple pieces of complex equipment surround a sedated and immobilized patient to perform the surgical care. This is additionally the case during minimally invasive surgical procedures wherein sophisticated medical imaging devices and graphical displays are relied upon by the caregivers to monitor the process and performance of the procedure without the need for a large incision into the patient's body for direct visual inspection and guidance.

Audio and video systems in a surgical suite have been known or suggested although these have been limited in function and use. Video cameras in surgical suites have been used for external communication, for example for educational, training, or demonstration purposes. Video cameras have also been used as a passive documentation of the procedure for reference in the event of a later claim of liability. Audio and video systems have further been used for inter-procedure video conferencing for consultation purposes. Audio based command systems have further been suggested as a means for promoting sterility in the surgical suite by limiting physical interaction between care providers and medical devices.

However, improved surgery procedure performance, integration between medical devices and clinician users of those devices, as well as management of personnel and resources within the hospital of which the surgical suite is a part can be achieved but with greater leverage and integration of surgical suite audio and video resources.

BRIEF DISCLOSURE

In an exemplary embodiment of a workflow assistance system for image guided surgical procedures, an interventional imaging system operates to move relative to a patient. The interventional imaging system further operates to acquire interventional images of the patient during a surgical procedure. A surveillance system is arranged about a surgical suite. The surveillance system produces surveillance data. A workflow controller processes the surveillance data to identify and locate surveillance subjects in the surveillance data. Surveillance subjects include clinicians, the patient, the interventional imaging system, and medical equipment within the surgical suite. The workflow controller provides operational commands to the interventional imaging system based upon analysis of the surveillance data.

In an exemplary embodiment of a method of workflow assistance, surveillance data is obtained. The surveillance data includes image data during a surgical procedure from a plurality of cameras distributed in a surgical suite. Interventional images of a patient are obtained using an interventional imaging system. Surveillance subjects are identified in the surveillance data. The surveillance subjects include clinicians, the patient, the interventional imaging system, and medical equipment within the surgical suite. The surveillance subjects are located within the surgical suite based upon the surveillance data. Operational commands are provided to the interventional imaging system based upon the located surveillance subjects.

BRIEF DESCRIPTION OF THE DRAWINGS

FIGS. 6A and 6B depict two exemplary embodiments of automated surgical logs.

FIGS. 8A-8C are exemplary embodiments of surgical suite and equipment schematic data as may be used by embodiments of the system.

DETAILED DISCLOSURE

Due to increases in the variety of procedures and the specialized equipment for procedures, image-guided medical procedures have become less predicable in terms of scheduling, functional operation, and device interactions within the room. Additionally, procedures, individualization of care for patients/cases, and specialization in the skill an training of medical staff further contribute to the potential combinations of personnel, skills, and equipment in a surgical procedure. In this context of increasing complexity, providers of surgical care must ensure safety of the patient and the surgical staff while also improving patient care with improved procedures, integration of medical technology, and adherence to protocol. Safe and quality care must also be provided in a manner that controls costs by efficient use of hospital resources including rooms, equipment, and staff.

Exemplary embodiments of the workflow assistance system described in further detail herein combine a computer vision system arranged and operated within a surgical suite with a robotic interventional imaging system as is used for image-guided medical procedures. From this combination, the workflow assistance system enables prevention of collisions of the interventional imaging system with the patient, medical staff, or other equipment located in the surgical suite. The movement of the robotic interventional imaging system can be adapted to the physical environment of the surgical suite and the current locations of the patient, medical staff, and other medical equipment. Behavior and control of the interventional imaging system can be contextualized as a function of the locations, roles, and actions of individual medical staff members, patient position, and other medical devices in relation to the interventional imaging system. Sterile zones around the patient and surgical field can be enhanced by with embodiments as disclosed herein by facilitating touch-free interaction between clinicians and complex surgical equipment through the identification and interpretation of clinician actions. Medical staff action can be automatedly identified, interpreted and recorded in a procedure log. Surgical suite and personnel scheduling can be enhanced through intra-procedure prediction of procedure phases and duration. Additionally, the workflow assistance system can provide consistency check and assistance or guidance either intra-procedure or post-procedure against comparative established medical practice or guidelines.

Details regarding these advantages and features will be described in further detail herein with respect to the Figures.

Figure 1:
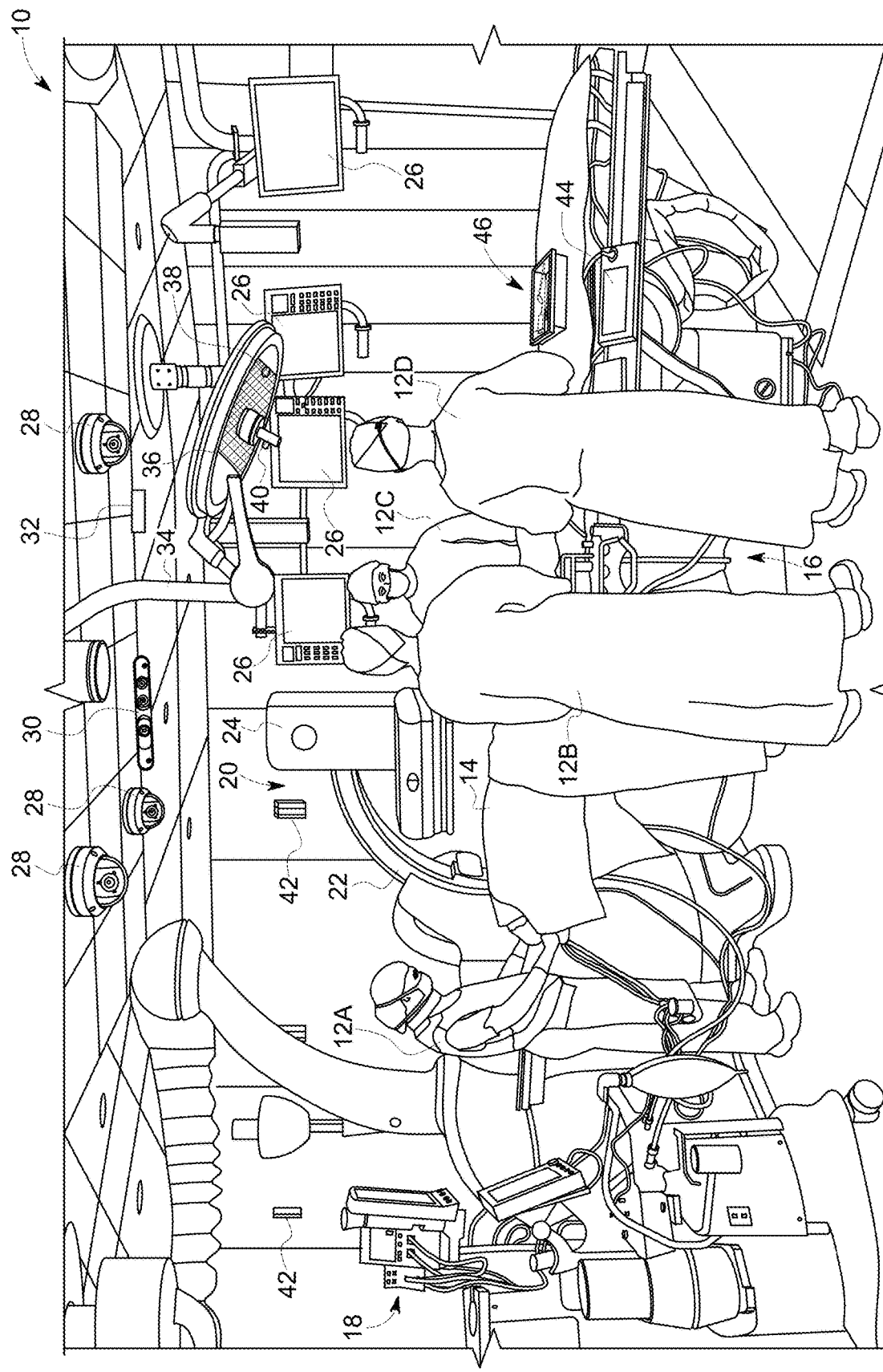
FIG. 1 depicts an exemplary embodiment of a surgical suite.

FIG. 1 depicts an exemplary embodiment of a surgical suite 10. A plurality of clinicians 12A-D work within the surgical suite 10 to surgically treat the patient 14. The clinicians 12A-D may exemplarily include an anesthesiologist/anesthetist 12A, a primary surgeon (and/or interventional radiologist or cardiologist) 12B and nurses or other support staff 12C, 12D. The patient 14 is supported by a table 16, the table 16 being operable to move translate and rotate the patient exemplarily in six degrees of freedom to position the patient 14 relative to the medical equipment and the clinicians in the surgical suite 10.

The surgical suite includes a variety of medical equipment used by the clinician's 12A-D to surgically treat the patient 14. An anesthesia delivery machine 18 is used by the anesthesiologist/anesthetist 12A to sedate and immobilize the patient 14. An interventional imaging system 20 is exemplarily used to acquire intra-procedure images of the patient at the surgical site. In an exemplary embodiment, the interventional imaging system 20 includes an imaging device 24, exemplarily and x-ray device mounted on a C arm 22 that is operated to position the imaging device 24 relative to the patient 14. It will be recognized that other imaging systems may be used instead of or in addition to the x-ray machine depicted in FIG. 1. These may include, but are not limited to endoscopes, ultrasound, or CT which may further provide images of the surgical site taken from within the patient 14.

The surgical suite 10 further includes a plurality of displays 25 which are adapted and arranged to present medical images of the patient, including, but not limited to those medical images obtained from the interventional imaging system 20. The displays 25 can also be adapted to present other medical data, for example pre-op lab results, a procedure plan, standard operating procedures, and checklists. It will be recognized that in embodiments, the interventional imaging system 20 may produce static images or dynamic images, for example fluoroscopic images. The images produced by the interventional imaging system 20 may be done so with or without the introduction of one or more contrast agents to the patient to facilitate imaging. Those images, as well as other images of the patient through previous imaging procedures or models developed therefrom may also be presented on the graphical displays 26. As will be detailed further in the present disclosure, the surgical suite 10 is provided with a plurality of cameras arranged about the surgical suite 10 in order to acquire intra-procedure images of the people, equipment, and activity within the surgical suite 10. The cameras exemplarily include pan-tilt-zoom (PTZ) cameras 28 which may exemplarily be mounted on the ceiling of the surgical suite 10. PTZ cameras are controllable to provide the functions of panning the cameras view, tilting the orientation of the camera, and zooming in on an area within the view of the camera. The cameras included in the surgical suite 10 may also include one or more depth cameras 30. The depth cameras 30 are provided with two or more camera sensors so as to provide stereoscopic as well as range, position, or location determination capabilities therefrom. In a further embodiment of the depth camera 30, an infrared (IR) light based camera is combined with an RGB visible light camera to provide the depth determination functionality. Other depth sensing cameras need only use one camera sensor combined with time of flight measuring capability, for example light detecting and ranging (LIDAR). Additionally, a thermal imaging camera 32 may be provided within the surgical suite 10. A thermal imaging camera 32 can provide patient or clinician positional information, particularly as the patient may be obscured in other camera images by shrouds and or blankets while the exact position of clinicians or parts of clinicians (e.g. arms, hands, heads) may be obscured by the protective garments worn by the clinicians.

The surgical suite 10 may further include one or more booms 34 to which equipment is articulably mounted. An example, a light 36 may be mounted to the boom 34. A camera 38 may further be mounted in conjunction with the light 36 and articulable with the boom 34. In such a manner, a camera 38 is provided with a field of view in the direction as the light used for illumination of the surgical area.

In additional exemplary embodiments as described in further detail herein, one or more microphones are further arranged within the surgical suite 10. A microphone 40 may be exemplarily a directional microphone and may also mounted in connection with the light 36 and camera 38 such that the directional microphone 40 is pointed towards the surgical site. Additionally, microphones 42 may be arranged about the surgical suite 10. With the use of two or more microphones, direction and location of speakers in recorded audio data can be identified. Apart from system design for audio based instruction or commands to medical devices, the microphones, as will be described in further detail herein, can provide additional contextual information regarding the actions of the clinicians during the procedure or the progress of the procedure.

Additionally, as depicted in FIG. 1, user interfaces 44 may be arranged at locations accessible to one or more clinicians 12A-D and configured to receive clinician inputs in order to control medical devices, the table 16, or the display of medical image data at one or more of the graphical displays 26. Additionally, during a surgical procedure one or more trays or containers of surgical supplies 46 are provided in proximity to the patient 14 and the clinicians 12A-D. The surgical supplies may include reusable instruments, but may also include consumable and or implantable supplies including sponges, gauze, catheters, guidewires, stents, screws, or other supplies as will be recognized by a person of ordinary skill in the art.

Figure 2:
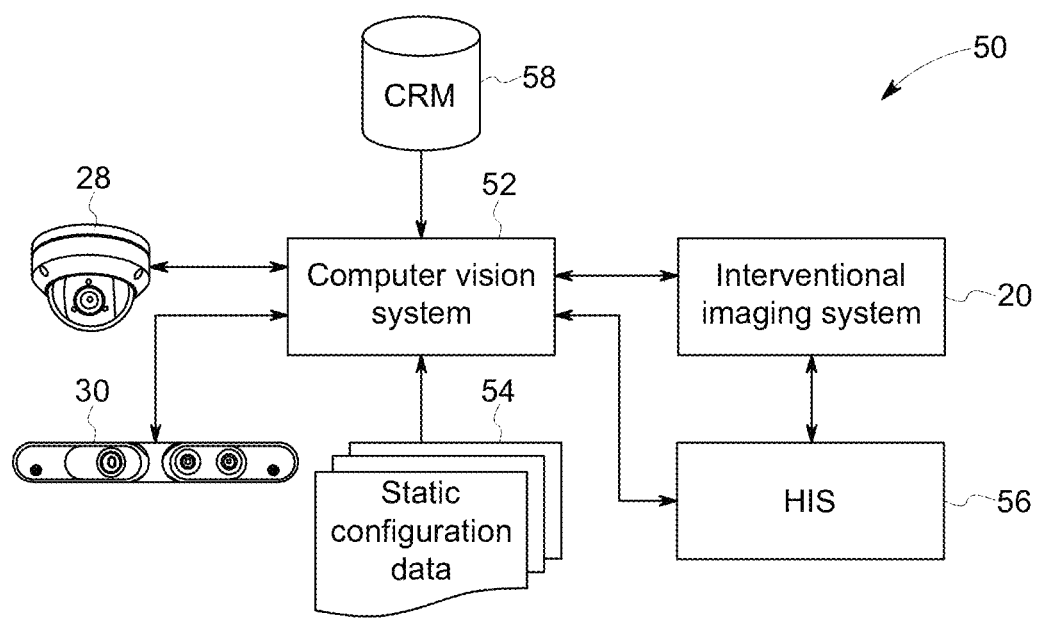
FIG. 2 is a system diagram of an exemplary embodiment of a computer vision workflow assistance system.
Figure 8A:
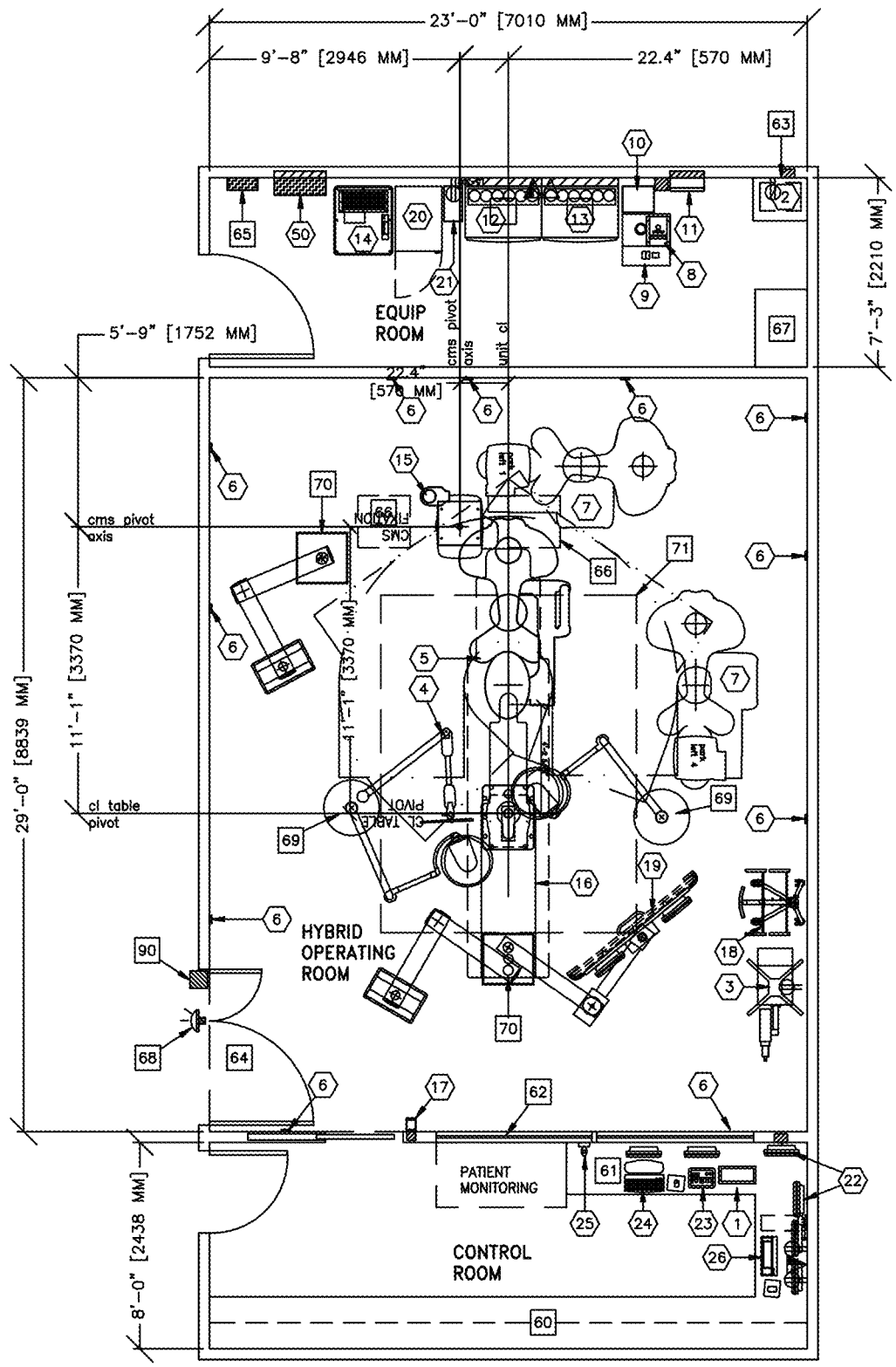
Figure 8B:
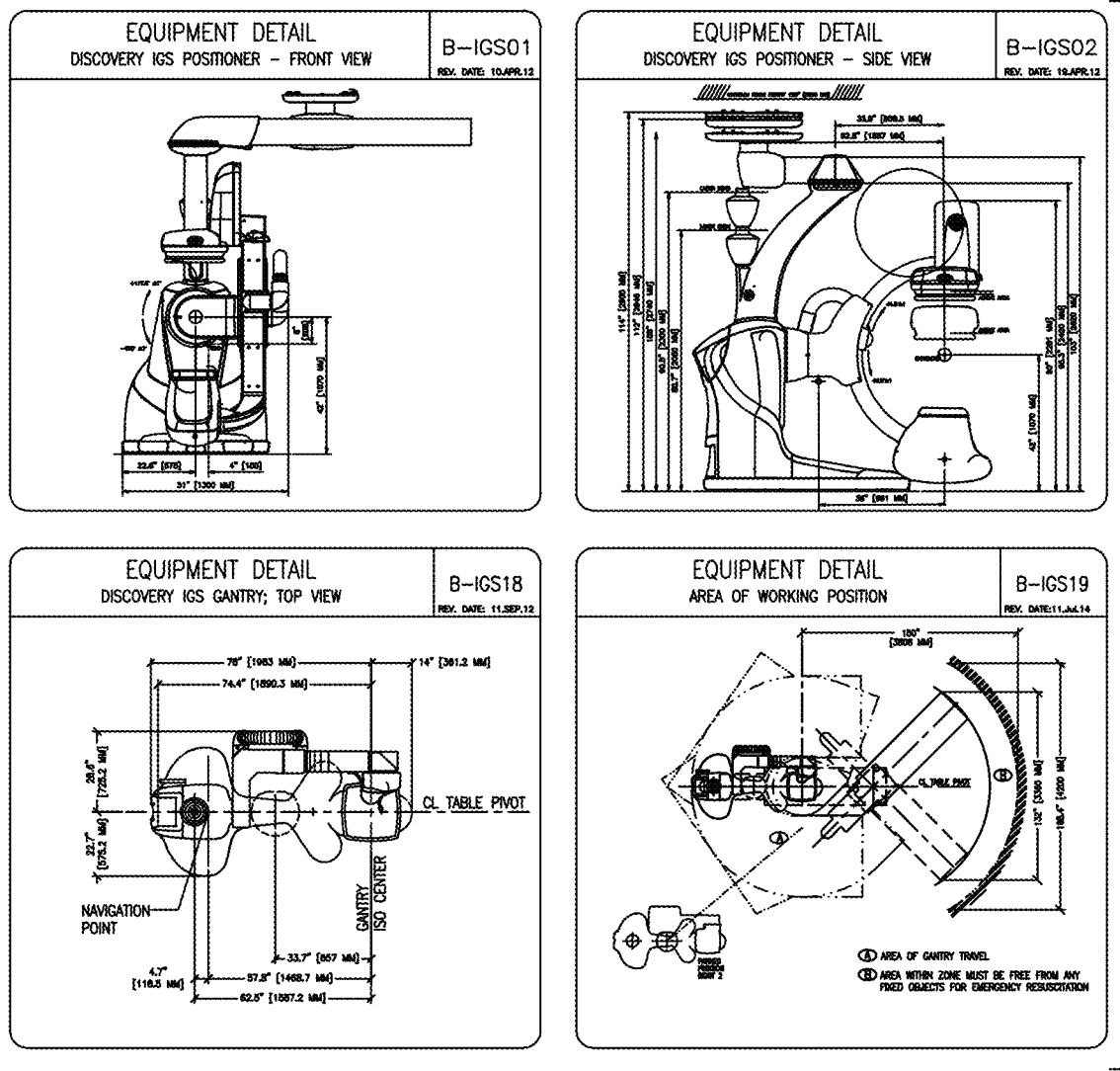

FIG. 2 is a system diagram of an exemplary embodiment of a workflow assistance system 50. The workflow assistance system 50 includes a computer vision system 52 which is communicatively connected to one or more cameras, including a PTZ camera 28 and/or a depth camera 30. The computer vision system may exemplarily be embodied on a dedicated computer with a general processing unit or may be integrated into other hospital computer systems and operated within another hospital computing system. The computer vision system 52 receives static configuration data 54 which aids the computer vision system in analyzing and interpreting the image data obtained from the cameras 28, 30. The static configuration data 54 may include geometric information regarding the surgical suite and/or various equipment known to be located within the surgical suite. FIGS. 8A-8C exemplarily depict this geometric information in the form of schematic drawings that may be used by the workflow assistance system. The geometric information may include, but is not limited to CAD drawings or models of medical equipment located within the surgical suite.

FIG. 8A is an exemplary schematic drawing of a surgical suite which provides geometric information regarding the dimensions and layout of the equipment within the surgical suite. This information can provide a contextual basis and initial assumptions regarding the position equipment within the surgical suite. The geometric data can be used in combination with the ranging or other depth sensing capabilities to determine distances and orientations between people and equipment. FIG. 8B depicts exemplary schematic drawings of medical equipment that may be located in the surgical suite. This may include aesthesia delivery machines, interventional imaging systems, patient support tables. The CAD drawing may further by adapted or apended with medical device kinematic data, for example with respect to robotic medical devices, which may include, but are not limited to surgical robots or interventional imaging C-arm movements.

The non-limiting examples of static configuration data provided in FIG. 8B include CAD schematic diagrams of an interventional imaging system. The schematic diagrams exemplarily present the size, shape and measurements of the interventional imaging system and associated gantry positioner in top, front, and side views. A kinematic diagram exemplarily shows the operational working position area of the interventional imaging system relative to a patient support table. It will be recognized that while schematic information regarding an interventional imaging system is shown in FIG. 8B, that the static configuration data may include similar information regarding any other pieces of medical equipment that may located and/or used within the surgical suite. The dimensions, device shapes, and kinematic information in the static configuration data can be used by the computer vision system to aid in the identification of medical equipment in the surveillance data, and also to determine operational commands, warnings, or guidance based upon detected or predicted medical equipment movement.

FIG. 8C provides still further examples of static configuration data, represented as radiation scatter plots relative to schematic diagrams of an interventional imaging system and patient support table. FIG. 8C exemplarily provides top and side views of the interventional imaging system and the associated radiation scatter plots based upon emitter position settings. This provides an additional example of operational data regarding particular pieces of medical equipment that may be received and processed by the computer vision system as static configuration data in accordance with the present disclosure. Exemplary embodiments of the operation of the computer vision system to exemplarily use the radiation scatter plots will be described in further detail herein.

Referring back to FIG. 2, the static configuration data 54 may be stored in a computer readable medium that is communicatively connected to the computer vision system 52. In one embodiment, the static configuration data 54 may be provided to the computer vision system 52 during a start up, calibration, or initialization procedure of the computer vision system prior to the surgical procedure. Or in another embodiment, the static configuration data 54 may be accessed by the computer vision system 52 upon detection of one or more pieces of medical equipment within the surgical suite. Detection of various pieces of medical equipment may be done so by image recognition analysis and processing of the image data received from the cameras 28, 30 or medical equipment may be provided with a barcode or quick response (QR) code within the field of view of one or more of the cameras 28, 30 so that image analysis of the image data from one or more of the cameras 28, 30 can include identification and interpretation of the barcode or QR code which identifies static configuration data 54 to be accessed and used by the computer vision system 52.

The computer vision system 52 is further communicatively connected to the hospital information system (HIS) 56. The HIS 56 exemplarily provides the computer vision system 52 with anonymized (non-image) workflow information. For example, information which may be obtained from one or more of the medical devices located and in use within the surgical suite. The HIS may also provide a list and identification of personnel expected to be in the surgical suite as well as an identification of the roles or tasks assigned to these individuals. In still further exemplary embodiments, the HIS system may provide identifying information for each of the assigned clinicians which may include, but is not limited to digital models of the clinicians and/or photographs of the clinicians. The HIS 56 further may include scheduling, procedure log, and consumable log information which are provided to the computer vision system to inform the computer vision system regarding an expected procedure to be performed in the surgical suite, and an expected process to the scheduled procedure, and expected consumable use during the procedure. The HIS may further include procedure guidelines, for example personnel and equipment spacing, expected duration, procedural milestones, radiation dose, contrast agent quantities, and supply requirements. These procedural guidelines may be used as described in further detail herein for the analysis and evaluation of the current surgical procedure against guideline or recommendation action.

The computer vision system 52 is further communicatively connected to the interventional imaging system 20. The interventional imaging system 20 may exemplarily provide gantry and or table positions. These positions may be internal positions (e.g. the detector array of the imaging system is at a position two inches above a default or neutral position or the C-arm is rotated to an angle of 20 degrees). The positions of the gantry and the table may be external positions, which may be determined or reported as relative positions between identified objects, people, or locations. External positions may also be determined and reported in reference to a positional grid or coordinate system overlaid on the surgical suite area or volume. In a relative position system, positions may be determined or reported for example as the detector of the imaging system is 18 inches from the surface of the table. Relative positions as just described may be determined by the computer vision system or the medical equipment itself based upon position and/or proximity sensors located within the medical equipment. The interventional imaging system 20 may further include a CAD or dynamic CAD model of the medical equipment itself and provide this information to the computer vision system 52. The CAD or dynamic CAD model may be further used for determination and calculation of either internal or external positions.

As will be noted in further detail herein, the computer vision system 52 operates to receive the static configuration data 54 and hospital data from the HIS 56 and imaging system or receives the static configuration data 54 from the interventional imaging system 20. The computer vision system 52 uses this static configuration data 54 to analyze and interpret image data collected form the cameras 28, 30 in order to provide operational commands in the form of instructions or controls to improve procedure workflow for the clinicians. In an exemplary embodiment, the computer vision system 52 interprets the image data from the cameras 28, 30 in view of static configuration data 54 regarding the geometry of the surgical suite itself and the medical equipment itself in further combination with the data from the interventional imaging system 20 in order to identify and avoid collision risks between equipment and personnel, the collision risks may be avoided by providing operational commands to the interventional imaging system, for example to define a virtual gantry about the patient or identify portions of medical equipment movement ranges in order to avoid collision risks. Still further embodiments may include movement or trajectory instructions or instruction modifications in order to prevent or avoid collision with equipment, the patient, or clinicians. In a further exemplary embodiment, the computer vision system 52 uses image processing techniques and analysis to interpret procedural steps and events in the image data. These procedure steps and events may be recorded in an automatedly generated procedure log which is provided to or stored at the HIS 56.

Still further exemplary embodiments of functionality provided by embodiments will be described herein with respect to FIG. 3 which depicts a more detailed embodiment of a workflow assistance system 60. Like reference numerals are used between the Figures to indicate like components and the embodiments as described herein are merely exemplary and still further embodiments within the scope of the present disclosure may include more or fewer components then those as depicted and described herein. It will also be recognized that the embodiment description provided herein is for merely exemplary purposes and that other configurations of similar components may be recognized by a person of ordinary skill in the art in view of the present disclosure.

In addition to the features highlighted above with respect FIG. 2, the workflow assistance system 60 incorporates a plurality of sources of surveillance data and processes the different sources of surveillance data with an artificial intelligence enabled controller 62. The AI enabled controller is exemplarily a general purpose computer that has been programmed with computer readable code in order to operate, when the code is executed to use one or more artificial intelligence techniques in interpreting the surveillance data from multiple surveillance data sources in order to analyze and interpret the surveillance data to identify particular actions and event undertaken in the surgical procedure. In an exemplary embodiment, the AI enable controller 62 further includes or is communicatively connected to a machine learning module or machine learning system whereby machine learning techniques may be used to enhance surgical procedure analysis and interpretation over time as the AI enabled controller 62 processes subsequent surgical procedures.

While the computer visions stem 52 has been discussed above, it is to be recognized that in addition to the PTZ camera 28 and the depth camera 30 as described above, that the computer vision system 52 may receive image data from a heat sensing or thermal camera 64. As previously noted, the thermal image data can provide additional context in the event that patient and/or clinician bodies are obscured by shrouding or garments.

As noted above, the system 60 includes a plurality of surveillance data sources including and in addition to the image data processed by the computer vision system 52. In further embodiments, a sensing system 66 receives surveillance data from wearable devices 68. Wearable devices may include motion/activity trackers, which may include position determination systems. Position determination systems may include, but are not limited to global positioning system (GPS) and wireless triangulation. In other embodiments, the wearable devices may include a wearable radiation dose meter. In such an embodiment, information from the dose meter combined with other information tracked from the system can be used to provide an operator radioprotection recommendation, for example adjusting the staff position behind a shield. This may also be used in monitoring compliance with worker's health standards. In still further embodiments, the wearables include computerized glasses, for example mixed reality or augmented reality glasses, including, but not limited to Google Glass or Microsoft Hololens products. Both of those wearable products include outwardly facing cameras and therefore in addition to position and/or orientational surveillance data, image data may be acquired from these wearable devices as well. The wearable devices provide an additional contextual component which can be used to interpret clinician movements or actions. For example, a clinician line of sight can be inferred from the field of view of a camera on a wearable eyeglass device. A wearable worn at the hand or wrist of a clinician can provide positional information related to the motions of the clinicians hands and/or positions of the clinicians hands. The sensing system 66 receives the data available to the sensing system 66 from the wearable devices 68 and processes this information in a manner as needed to provide data to the AI enabled controller for interpretation and response.

In an exemplary embodiment, the AI enabled controller 62 operates to produce an estimate of clinician and/or patient radiation exposure or cumulative dose. As noted above, the static configuration data may include radiation exposure maps representative of radiation exposure during operation of an interventional imaging system. Similar radiation exposure information for other imaging systems or radiotherapy devices may also be available within the static configuration data. The AI enabled controller 62 can use those plots in combination with information regarding operation and settings of the interventional imaging system and determined locations of the clinicians and patient to calculate effective radiation doses during the surgical procedure. In an embodiment, current surgical procedure radiation dose information can be combined with clinician and/or patient cumulative dose information, for example as tracked in a hospital information system, to evaluate a lifetime cumulative dose. In still further embodiments, the estimations of radiation dose based upon radiation plots and clinician/patient position can be refined based upon data acquired from each clinician/patient equipped with a radiation dose meter wearable device. In an exemplary embodiment, depending upon the determined procedure or cumulative radiation dose, intra-procedure or inter-procedure guidance may be provided by the AI enabled controller 62 to warn a clinician regarding clinician or patient radiation dose, or to suggest radiation dose remedial actions, for example use or adjustment of a radiation screen.

A still further example of a surveillance system is an audio system 70 which is configured to receive audio data from a plurality of microphones 72. As noted above, the microphones 72 may be fixed in locations about the surgical suite or may be incorporated into another medical device or movable about the surgical suite, for example on a boom. The microphones 72 may include omnidirectional microphones and/or directional microphones. In still further embodiments, the microphones may include one or more steerable directional microphones or microphone arrays. The microphones 72 provide audio data to the audio system 70 interpretation and processing before the data is provided to the AI enabled controller 62. The audio system 70 may exemplarily process the audio data in a number of ways to obtain additional context regarding the actions and events occurring in the surgical suite in performance of the surgical procedure. Audio data may be interpreted through speech recognition processing and techniques for the communicative content of the audio data itself, for example to interpret the discussion between clinicians in order to identify actions or events in the surgery procedure. Additionally, in one embodiment, one or more clinicians may be tasked with the job of narrating the surgical procedure so as to provide an audio record of the procedure, which may later be processed into a text, or other data form, record of occurrences or events in the surgical procedure. In still further embodiments, rather than the content of the audio data itself, the audio data collected from a plurality of omnidirectional microphones and/or various directional microphones can help to locate particular clinicians within the surgical suite and to enhance and verify clinician location determinations made upon the basis of the image data or wearable data. In a still further embodiment, the audio system 70 can provide the AI enabled controller 62 with an audio map of the location and/or intensity of sound sources above a predetermined threshold. This audio map can be used by the AI controller 62 to associate sound events to particular individuals or machines identified by the video system.

In this manner, the surveillance data as provided by the computer vision system 52, sensing system 66, and audio system 70 is provided to the AI enabled controller 62 and the AI enabled controller 62 processes this information in accordance with the description herein to carry out various functions of the system 60.

As described above, the AI enabled controller 62 exemplarily has communicative access to the static configuration data 54. Although not depicted in FIG. 3, it will be recognized that any of the computer vision system 52, sensing system 66, and/or audio system 70 may also have communicative access to the static configuration data 54 as may be needed to facilitate the collection and processing of these respective forms of surveillance data. The static configuration data 54 provides the dimensional and/or geometrical data regarding the surgical suite itself and/or any medical equipment within the surgical suite, particularly those pieces of medical equipment which are movable and/or robotic in nature and thus may be expected to move during the course of the surgical procedure. Exemplary and non-limiting types of robotic medical equipment which may be found in the surgical suite may include an interventional imaging system C-arm, a patient support table, or a surgical robot, for example to insert and/or otherwise position a needle, for example for insertion of a catheter or guidewire into a patient. Access to the static configuration data by one or more of the subsystems may be as a result of clinician input during a set up or calibration phase prior to the surgical procedure while in other embodiments, the computer vision system may use image recognition to identify one or more pieces of medical equipment or to read a barcode, QR code, or other visual identifier located on the medical equipment within the field of view of one or more of the cameras to identify the medical equipment such that the appropriate static configuration data is accessed and used for analysis and interpretation of the surgical procedure.

In a still further exemplary embodiment, the AI enabled controller is communicatively connected to the interventional imaging system 20. In an exemplary embodiment, the interventional imaging system 20 itself may provide an identification of itself to the AI enabled controller 62 and the appropriate static configuration data obtained. Similarly, other medical equipment 74 within the surgical suite may also be communicatively connected to the AI enabled controller 62. The other medical equipment 76 may similarly provide its own identification to the AI enabled controller 62 for acquiring the appropriate static configuration data 54. In addition to identification information, the interventional imaging system, which may exemplarily be interventional x-ray, fluoroscopy, or a cone beam computed tomography (CBCT) machine or other interventional imaging devices can provide those interventional images to the AI enabled controller 62. In a still further exemplary embodiment, the interventional imaging system is positioned within the patient, for example as an endoscope an image data from inside the patient is acquired in this manner as well. As will described in further detail herein, the AI enabled controller 62 may combine the contextual data of the interventional imaging system showing the surgical site within the patient with the surveillance data acquired at the same time external to the patient in order to identify actions and events in the surgical procedure and carry out the functions as described in further detail herein. The AI enabled controller 62 is further exemplarily communicatively connected to the hospital information system (HIS) 56 through which the AI enabled controller 62 is able to access surgery, personnel, or surgery suite schedules, surgical procedure logs, patient care guidelines, and procedure standards. In exemplary embodiments, the AI enabled controller 62 is able to read from and write to these data files associated with the hospital information system 56.

It will be recognized that in the above description, the AI enabled controller 62 has been depicted as a stand alone component. However, it will be recognized that in other embodiments, the functionality of the AI enabled controller may be performed at the same processor and/or computing system as the computer vision system and/or the interventional imaging system 20. It will be recognized that in embodiments each of the computer vision system 52, sensing system 66, audio system 70, AI enabled controller 62, and interventional imaging system 20 may operate as stand alone devices and execute as separate processors or computer systems. However, it will be also recognized that any combination of one or more of these components may be implemented on a single processor or computer system and in such a case some or all of these functions as described above and as further described herein may perform by such a device while remaining within the scope of the present disclosure.

Figure 3:
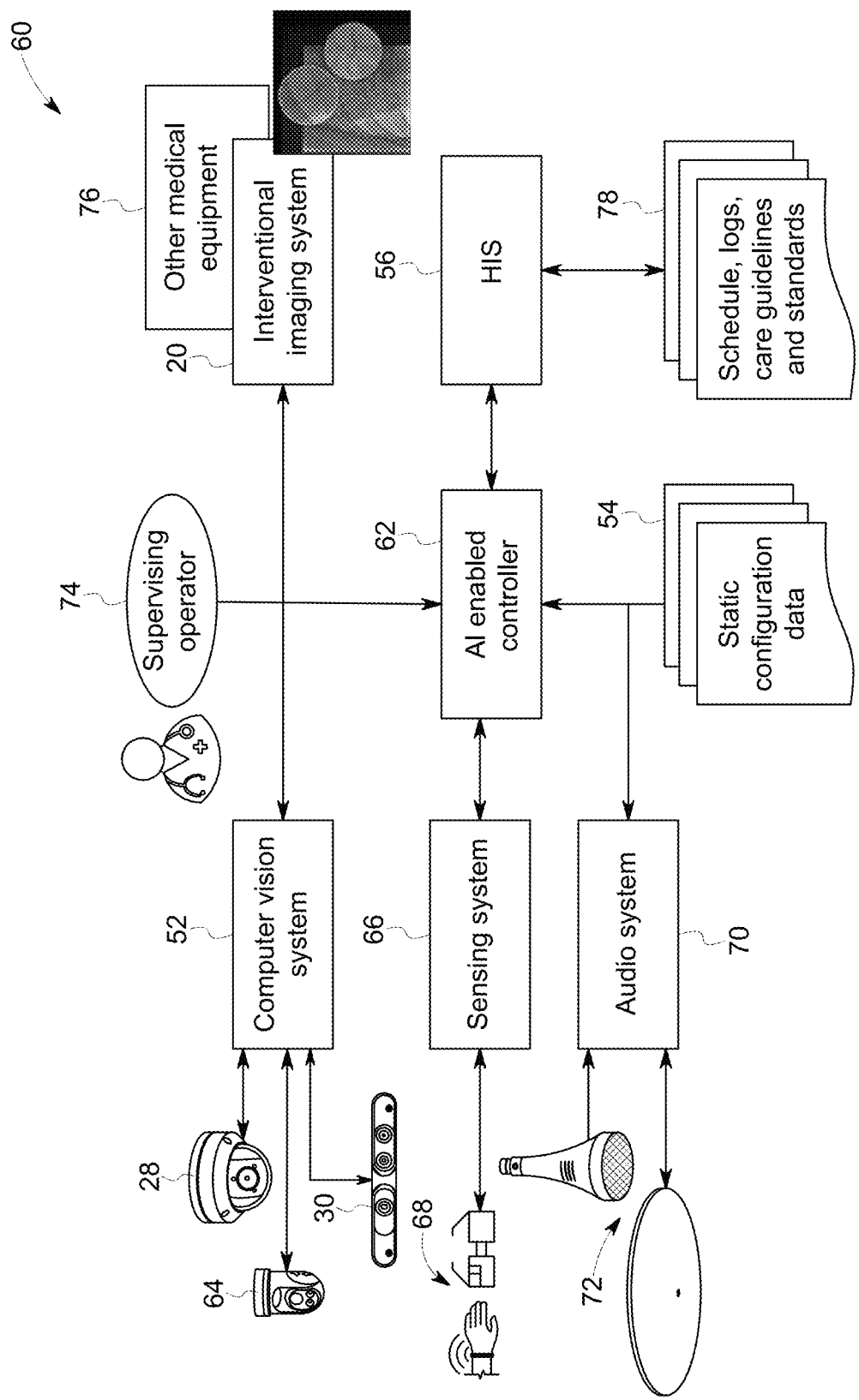
FIG. 3 is a more detailed block diagram of an exemplary embodiment of an integrated input workflow assistant for image guided procedures.

The workflow assistance system 60 as depicted and described with respect to FIG. 3 may exemplarily operate to carry out a variety of functions within the scope of the present disclosure. These functions include, but are not limited to collision avoidance between the interventional imaging system and other medical equipment and/or clinicians. Automated medical equipment operation or instruction as a function of surgical procedure context, automated procedure logging, predictive scheduling, and a standard of care evaluations.

The system 60 may operate to acquire and analyze real-time geometry information regarding the position and orientation of various equipment, clinicians, and the patient within the surgical suite. The computer vision system 52 can operate to detect these objects in the image data acquired from one or more cameras. Analysis of this real-time geometry information in the image data from the cameras enables the AI enabled controller 62 to anticipate medical equipment collisions with other medical equipment (e.g. the table), clinicians, or the patient. Once these potential collisions are anticipated, interventional imaging system movement trajectories may be calculated and instructed in order to avoid obstacles. Alternatively, alarms may be enacted. In a further embodiment, the speed of movement of the robotic medical equipment may be slowed during movement within areas of high potential for collisions. In an exemplary embodiment, the computer vision system 52 may receive static configuration data 54 comprised of a priori information relative to the medical equipment, for example in the form of CAD drawings and/or medical equipment kinematics. The computer vision system 52 may use image processing and detection techniques to determine exact position, orientation, or shape of the medical equipment, clinicians, or patient from the image data provided to the computer vision system 52.

In an embodiment, medical equipment, including interventional imaging system equipment may be marked with barcodes and/or QR codes in a location conspicuously within the field of view of one or more of the cameras and thus captured within the image data provided to the computer vision system 52 from one or more cameras. In the image data, the barcode or QR code may be read and, in an exemplary embodiment, the identification of the medical equipment provided by the barcode or QR code is used to access and receive CAD and/or kinematic data regarding the identified medical equipment. In further exemplary embodiments, the clinician can be tracked by recognition and computer vision determination techniques. As previously mentioned, the position of the patient may be determined and/or refined using a thermal or terahertz type camera which can provide indications of the actual body position and/or shape of the patient through any medical shrouds, garments, or drapes. As the computer vision system 52 can follow multiple objects in time throughout the operating, the computer vision system 52 can infer possible obstacles within the surgical suite even if an object is not in direct line of sight of one or more cameras connected to the computer vision system 52.

The AI enabled controller 62 may use the data received from the computer vision system 52 indicating the positions of medical equipment, clinicians, and the patient within the surgical suite and the AI enabled controller 62 may use this information to determine and provide operational commands to the interventional imaging system 20 or other medical equipment 76. The AI enabled controller 62 operates to automatedly provide inputs to the interventional imaging system 20 based upon the position of the clinicians in the surgical suite, a gaze or clinician attention direction, a position of the imaging system relative to the patient and/or another piece of medical equipment, currently ongoing functions of the interventional imaging system or other medical equipment.

In a further exemplary embodiment, the AI enabled controller 62 provides additional automated operational controls to pieces of medical equipment within the surgical suite. The AI enabled controller 62 can provide operational controls to graphical displays to adjust user interface or display configurations based upon a determined current surgical procedure step, recent procedure event, or predicted upcoming procedure step or event. These operation controls may include a prompt or suggestion in a user interface to perform or set up a particular function or operation of a piece of medical equipment. In an embodiment, the AI enabled controller 62 may provide operational controls to an interventional imaging system to set up operational parameters for a predicted next imaging function. As an example, the operational controls may select an imaging protocol as a function of an anatomy of the patient to be imaged, e.g. a head, a chest, an abdomen, or a leg.

In another example, the AI enabled controller 62 may analyze the surveillance data related to the patient and provide operational controls based upon this analysis. The patient orientation may be identified from the surveillance data and automatedly provide this information to the imaging system 20, the HIS 56, or store this information accessible to the AI enabled controller 62 for later referral and use. In a still further embodiment, the surveillance data that pertains to the patient may be analyzed by the AI enabled controller to build a personalized anatomical model of the patient. This personalized anatomical model may be further stored in a manner accessible by the AI enabled controller for use in imaging system collision detection and mitigation. The AI enabled controller 62 may further use a personalized anatomical model of the patient to determine patient radiation dose.

In a further example, the AI enabled controller 62 may provide operational controls to one or more of the graphical displays based upon an identified clinician, the clinician's location, the clinician's gaze direction, and/or a detected procedural step or event. The operational controls may configure the graphical display to present information relevant to the actions performed by a particular clinician in view or looking at that graphical display. The AI enabled controller 62 may also provide operational controls to a wearable device associated with one of the clinicians to exemplarily provide the intra-procedure guidance as discussed within the present disclosure.

In still further exemplary embodiments, a progress through the surgical procedure may be determined based upon the positions of the clinicians or the identification of surgical objects and/or the hands of the surgeon relative to a surgical site on the patient. Further examples of automated system operation or input include dose management to the clinicians, contextual controls of medical equipment, automatic selection of imaging protocols as a function of patient body part being imaged, automatic configuration of displays, and others as will be recognized by a person of ordinary skill in the art in view of the present disclosure.

Additionally, the computer vision system 52 may operate to further infer behavior and intent of the clinicians. This may exemplarily be performed with assistance of the AI enabled controller 62 and machine learning techniques in the examples given, the behavior and intent of the clinicians may be inferred from the observable and detectable actions of the clinicians in the image data processed by the computer vision system 52 or sensing system 66. This may include the determination of a clinician's direction of vision or a current position of the clinician's body or actions performed by the hands of the clinician. This may further include identification of surgical equipment currently handled by the clinician. This may be furthered by the audio data processed by the audio system 70 in which the clinicians may provide further context as to behavior or intent either through narration of the surgical procedure or intra-procedure discussion between the clinicians.

In still further embodiments, the system 60 may operate to process the surveillance data to extract semantics within the surveillance data by translating the surveillance data into meaningful events or actions in the surgical procedure. These may be an automatedly recorded in a procedure log which can be stored at the HIS 56. In this manner, beyond the patient, clinicians, and medical equipment, the interactions of these subjects may also be identified and tracked into the automated procedure log to provide an initial inventory of the surgical suite as to track surgical equipment and/or various consumables. Consumables may exemplarily be tracked in the automated procedure log based upon barcodes located on each of these items, the barcode or QR code being captured in the image data and read by the computer vision system 52. The use of medical equipment, surgical tools, or consumables by specific clinicians may be identified and documented from the surveillance data.

In still further embodiments, the surveillance data may also include the image data from the interventional imaging system 20 which may be provided directly from the interventional imaging system 20 or from the PACS system within the HIS 56. As with the image processing described above, further procedure action or event semantic information can be determined from the medical images of the interventional imaging system 20 for example, introduction of the guidewire to the surgical site, presence or deployment of a stent, balloon inflation, contrast injection, or other actions or events visible within the image data from the interventional imaging system 20. The action or event semantic information may further identify the anatomical location of the detected event (e.g. left atrium, right kidney) as well as a timestamp of when the action or event occurred.

In a still further exemplary embodiment, with the actions and events of the surgical procedure being identified and tracked, for example by a recording in the automated procedure log, the automated procedure log can be stored by the HIS or be communicated to the HIS and the HIS can use this recorded surgical procedure action and event data to provide predictive scheduling based upon the current actions and events identified in the surgical procedure. For example, patient out, room cleaning, room preparation, next patient in, and next procedure start events can all be estimated based upon known or modeled duration for these next scheduled actions within a surgical suite and predicted remaining duration in the current surgical procedure. Through identification and communication of the completion of each event in the surgical procedure in real time, this scheduling can be performed without the need for the presence of a coordinator. The surveillance data can be evaluated against models upon which the event duration estimates are based, depending upon changes, delays, or advancements of the actual event duration, the time to completion estimate for that event can be modified and the subsequent schedule adjusted forward or backwards. In still further embodiments, each remaining event in the surgical procedure can be predicted based upon surgical procedure models and/or historical data of prior surgical events through machine learning which may be performed by the AI enabled controller 62.

In a further embodiment, each surgical procedure is mapped into a series of actions and/or events that can be identified and tracked in the surveillance data, a guideline or preferred procedure can be established and each of the expected actions or events defined compared to the actions and events identified in the surveillance data. In this manner, each surgical procedure can be defined with established care standards, guidelines of expected actions or events, and workflow efficiency pattern guidelines. These standards and guidelines can be compared to the events and actions of the clinicians in the surveillance data and reported back to the clinicians, including with possible recommendations in real-time and/or offline. When made in real-time, the clinicians may be notified of procedural recommendations on a graphical display oriented within the surgical suite. In an offline recommendation, the recommendations may be presented in review or for training purposes.

Figure 4:
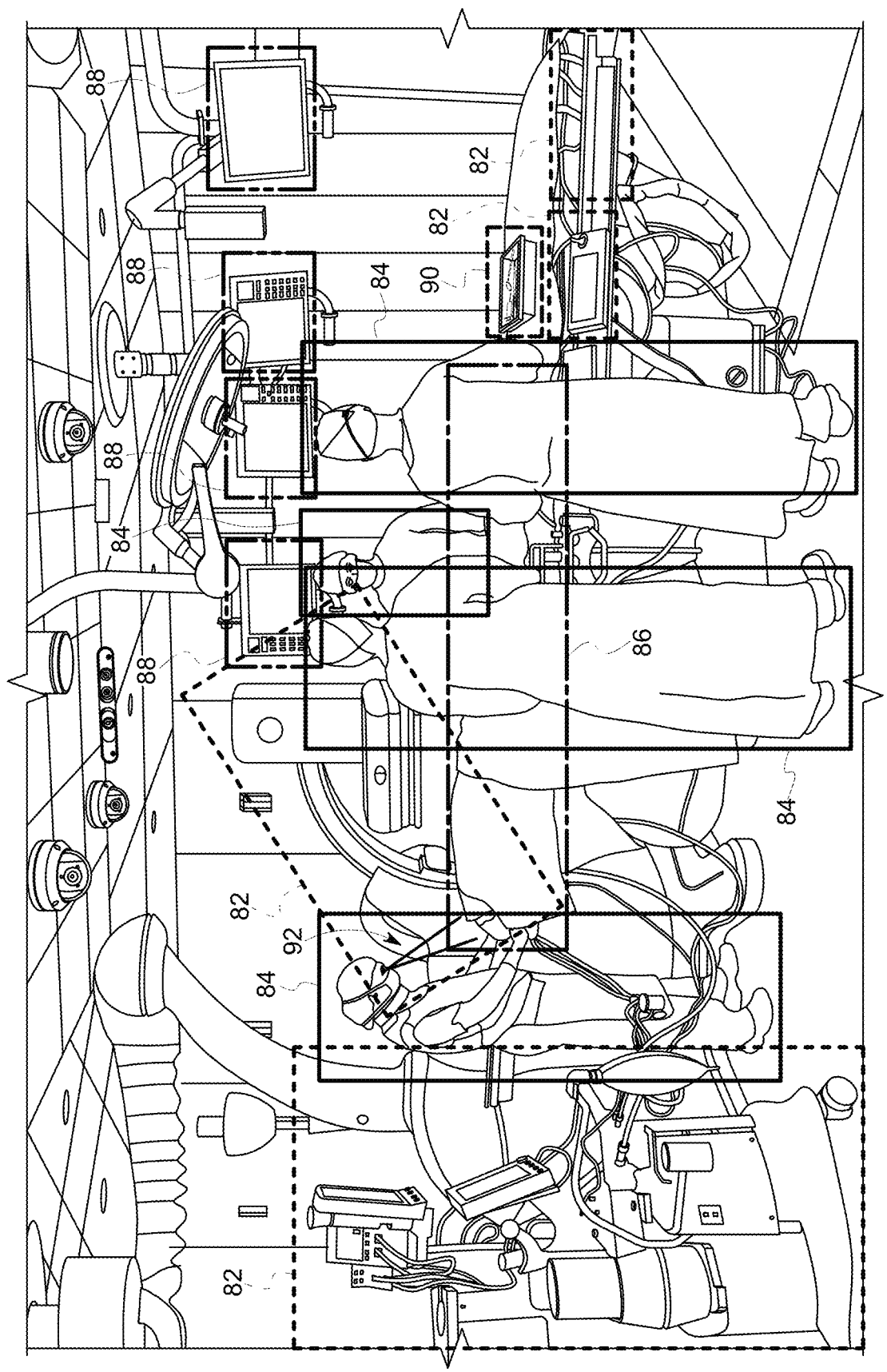
FIG. 4 depicts a view of a surgical suite with the results of automated object detection.

FIG. 4 depicts an exemplary embodiment of image data acquired of a surgical suite. In the image data, the computer vision system identifies each of the pieces of equipment, clinicians, or patient being tracked by the surveillance system in the surgical suite. The computer vision system identifies each of the subjects of surveillance in the obtained surveillance data. In the example of the surveillance data being image data, the identification is visualized exemplarily with contextual boxes. It will be recognized that in embodiments the subjects of surveillance may be identified and numerically or otherwise represented within the processing of the system as opposed to being visually presented as shown in FIGS. 4 and 5.

For example, in FIG. 4, the computer vision system can identify equipment 82. The equipment 82 may include an aesthesia machine, an x-ray C-arm, or equipment controls. At 84, the clinicians within the surgical suite can be identified. Each of the clinicians can be labeled. In an exemplary embodiment, the clinicians may be labeled based upon the order in which the clinicians are detected and given numbered identification e.g. operator number 1, operator number 2, etc. While in other embodiments the clinicians 84 may be individually identified, for example through the pre-detected presence of an identification code e.g. an identification code on a clinician garment or an RFID enabled identification badge or wearable personal dose meter with wireless connectivity. The patient can be identified at 86. Detection of the patient location can assist in avoiding any collisions between the C-arm and the patient or to provide context as to the anatomical locations upon which the clinicians are working. Monitors can be identified at 88. The monitors, if within the field of view of the collected image data can be analyzed to determine what information is currently being presented to the clinicians. This can be compared to procedure guidance or can provide further indication as to the actions being performed by the clinicians or current events within the surgical procedure. At 90, a location of surgical tools is identified. In an embodiment, and as will be described in further detail herein, a close up view including image data of the surgical tools 90 can provide for identification of the tools for example by detection of a barcode on each of the surgical tools to identify which tools are selected and used by the clinicians during the surgical procedure. As further depicted in FIG. 4, a clinician vision direction 92 can be identified from the position and orientation of the clinician's head and/or body. It will be recognized that in an exemplary embodiment wherein the clinician is provided with a wearable glasses device, that an orientation sensor or the image data collected from the wearable may further inform and refine a determination of vision direction 92.

Figure 5:
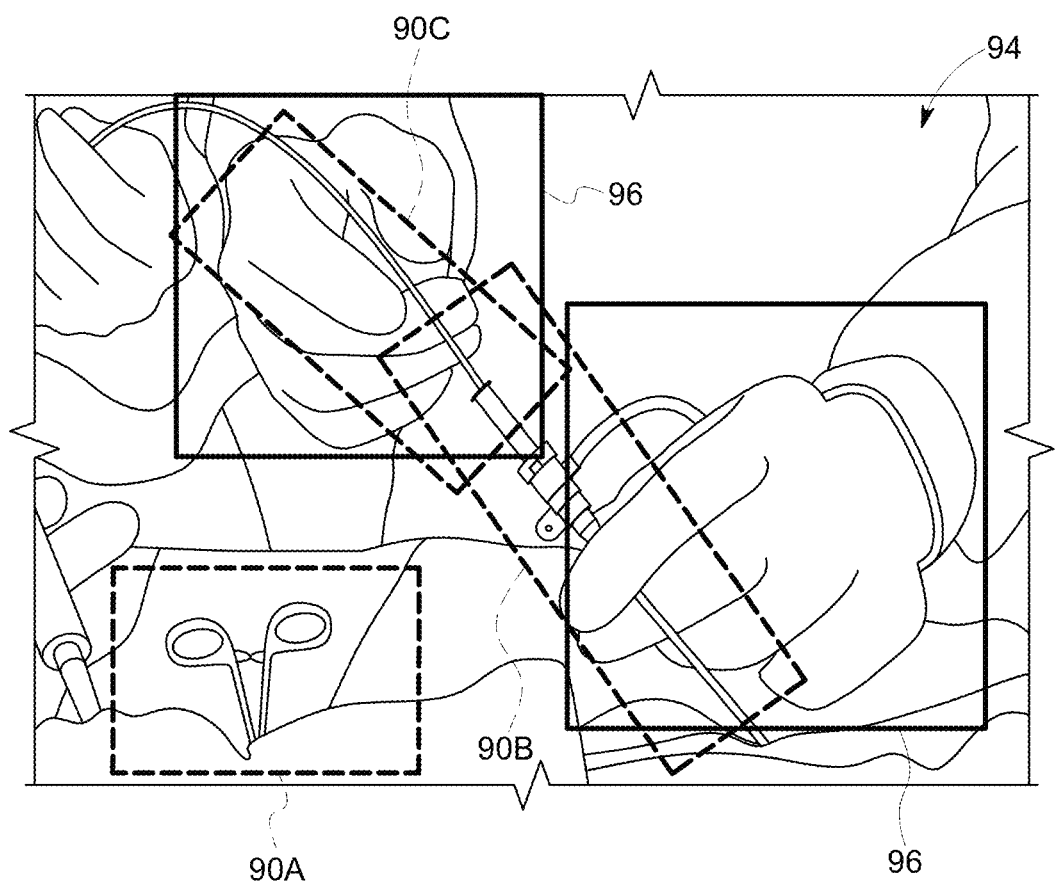
FIG. 5 depicts another view of exemplary video image data with the results of automated object detection.

FIG. 5 depicts further image data provided in a close up view 94. The close up image data may be acquired from one of the PTZ cameras zooming in on a specific location of interest, for example the surgical site or on a tray of surgical tools. In FIG. 5 further various objects are detected in the image data, including multiple surgical tools 90, including a clamp 90A, an introducer 90B, and a guidewire 90C. Additionally, clinician hands 96 are identified. In connection with the image data 80 depicted in FIG. 4, the clinician associated with the detected hands 96 can be known or identified. Therefore, for example from the image data 94 in FIG. 5, the use of the introducer 90B and guidewire 90C equipment by the clinician associated with detected hands 96 may be recorded or the event of introducing the guidewire into the patient may be recorded in a procedure log.

FIGS. 6A and 6B present two exemplary embodiments of procedure logs as may be automatedly produced in embodiments of the present disclosure. In FIG. 6A, the procedure log 98 is produced on an object by object basis and for example the objects listed in 6A as well those objects as those depicted and labeled in FIGS. 4 and 5. In the procedure log 98 each of the detected objects are identified at column 100. If a role or operation is inferred from the surveillance data this is presented at column 102. In the procedure log 98, subsequent columns 104 are produced at various time stamps or time intervals and include an action or event at that time associated with that detected object. Thus, the procedure log produces a record over time of the detected actions or events of each object being monitored in the surveillance data. In the procedure log 106 depicted in FIG. 6B, the procedure log 106 is a time stamp sequence of detected events or actions from the surveillance data. The procedure log 106 includes a time stamp 108 and an associated event 110 that is recorded at that time stamp. The procedure log 106 may create as many time stamps and events or action notations as needed to document detected actions and events within the surgical suite. As further shown in the procedure log 106 the procedure log may include for example clinician actions 112, procedure summaries and durations predictions 114, medical equipment movements or actions 116, scanning or identification of surgical tools 118, procedure events 120, or recommended actions to be taken 122. Each of these notations can be produced by the workflow assistance system as previously described through analysis of the surveillance data.

Figure 7:
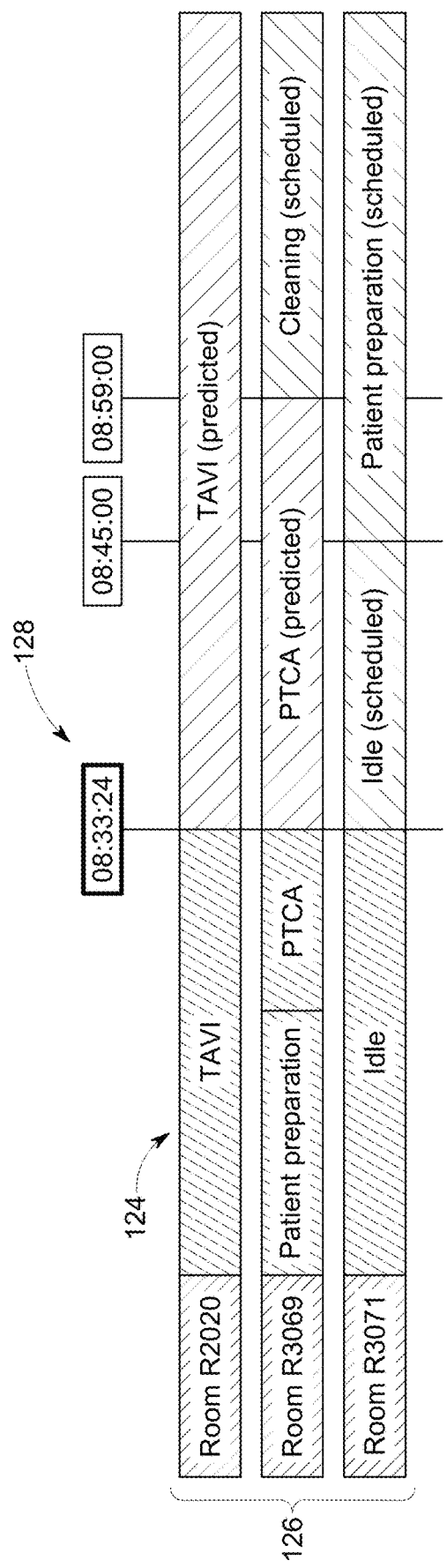
FIG. 7 depicts an exemplary embodiment of a visual display of surgical suite scheduling.

FIG. 7 depicts an exemplary embodiment of a scheduling table 24. In the scheduling table 24 each of a plurality of rooms 126 are identified and the current time 128 is indicated. Each room 126 is provided with the procedure or schedule status of that room as previously used and to the right of the indication of the current time 128, a prediction of the schedule for that room is made. The predications of the room use can be updated as predicted procedure completion times are updated during the course of the procedure. In this manner, the cleaning, room preparation, patient preparation, and start of the next procedure can all be updated based upon the estimated current procedure completion. In still further embodiments, the surveillance data may be acquired at other times beyond when the surgical procedure is performed such as to provide monitoring and tracking of room cleaning or room preparation. It will understood that similar concepts and techniques as described above with respect to tracking the surgical procedure can also be applied to the room cleaning and room preparation. In this manner, an updated prediction of when the room will be clean or when the next procedure can start can be predicted and updated based upon the actual steps and actions taken to clean and/or prepare a room. Similar guidance, logging, and quality assurance may be provided to the room cleaning and/or room preparation processes as described above with respect to the surgical procedures through the similar analysis of the surveillance data. In this exemplary manner, the surveillance data may be analyzed to identify and analyze the actions of many different types of personnel, including, but not limited to clinicians including doctors, surgeons, cardiologists, anesthesiologists, nurses, and cleaning staff In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A workflow assistance system for image guided surgical procedures, comprising:
   an interventional imaging system that operates to move relative to a patient and to acquire interventional images during a surgical procedure;
   a surveillance system arranged about a surgical suite, the surveillance system producing surveillance data;
   a workflow controller that processes the surveillance data to identify and locate surveillance subjects, the surveillance subjects comprising personnel, the patient, the interventional imaging system, and medical equipment, within the surgical suite based upon the surveillance data and provide operational commands to the interventional imaging system based upon analysis of the surveillance data;
   wherein the surveillance system comprises a plurality of cameras and the surveillance data comprises image data from the plurality of cameras; and
   wherein the workflow controller further receives static configuration data regarding the surgical suite, medical equipment, interventional imaging system or personnel and processes the surveillance data and the static configuration data to identify interactions between two or more surveillance subjects.

2. The workflow assistance system of claim 1, wherein the operational commands to the interventional imaging system are movement commands to avoid collisions between the interventional imaging system and the patient, personnel, and medical equipment in the surgical suite.

3. The workflow assistance system of claim 1, wherein the plurality of cameras comprises at least one pan-tilt-zoom camera, a depth camera, or a thermal camera.

4. The workflow assistance system of claim 1, wherein the surveillance system further comprises a plurality of microphones and the surveillance data comprises audio data.

5. The workflow assistance system of claim 1, wherein the workflow controller identifies locations and actions of the interventional imaging system and the personnel from the image data.

6. The workflow assistance system of claim 5 wherein the workflow controller comprises a learning engine that processes surveillance data from previous surgical procedures to interpret the surveillance data acquired during the surgical procedure.

7. The workflow assistance system of claim 1, wherein the workflow controller identifies locations and actions of the interventional imaging system and clinicians from the surveillance data and identifies surgical procedure events from the identified locations and actions.

8. The workflow assistance system of claim 7, further comprising a link to a hospital information system and the workflow controller automatedly records a surgical event log of the identified surgical procedure events and identified actions.

9. The workflow assistance system of claim 8, wherein the hospital information system predicts a surgical procedure duration from the surgical event log.

10. The workflow assistance system of claim 9, wherein the hospital information system adjusts a schedule of use of the surgical suite based upon the predicted surgical procedure duration.

11. The workflow assistance system of claim 7, wherein the workflow controller obtains at least one procedural guideline from a hospital information system and compares the procedural guideline to the identified locations and actions of the clinicians and the identified surgical procedure events to evaluate the surgical procedure and create clinician guidance.

12. The workflow assistance system of claim 1, wherein the surveillance system further comprises at least one wearable device associated with a clinician.

13. The workflow assistance system of claim 12, wherein the wearable device is a dose meter and the workflow controller obtains radiation level data of the interventional imaging system, calculates a radiation dose received by the clinician, and produces guidance to the clinician regarding dose mitigation.

14. A workflow assistance system for image guided surgical procedures, comprising:
- an interventional imaging system that operates to move relative to a patient and to acquire interventional images during a surgical procedure;
- a surveillance system arranged about a surgical suite, the surveillance system producing surveillance data;
- a workflow controller that processes the surveillance data to identify and locate surveillance subjects, the surveillance subjects comprising personnel, the patient, the interventional imaging system, and medical equipment, within the surgical suite based upon the surveillance data and provide operational commands to the interventional imaging system based upon analysis of the surveillance data;
- wherein the surveillance system comprises a plurality of cameras and the surveillance data comprises image data from the plurality of cameras; and
- wherein the workflow controller identifies locations and actions of the interventional imaging system and the personnel from the image data.

15. A workflow assistance system for image guided surgical procedures, comprising:
- an interventional imaging system that operates to move relative to a patient and to acquire interventional images during a surgical procedure;
- a surveillance system arranged about a surgical suite, the surveillance system producing surveillance data;
- a workflow controller that processes the surveillance data to identify and locate surveillance subjects, the surveillance subjects comprising personnel, the patient, the interventional imaging system, and medical equipment, within the surgical suite based upon the surveillance data and provide operational commands to the interventional imaging system based upon analysis of the surveillance data;
- wherein the surveillance system comprises a plurality of cameras and the surveillance data comprises image data from the plurality of cameras; and
- wherein the workflow controller identifies locations and actions of the interventional imaging system and clinicians from the surveillance data and identifies surgical procedure events from the identified locations and actions.

* * * * *